United States Patent [19]

Sauerbier et al.

[11] Patent Number: 4,990,675
[45] Date of Patent: Feb. 5, 1991

[54] PROCESS FOR THE PRODUCTION OF DISULFIDES

[75] Inventors: Michael Sauerbier, Altrip; Karl Nützel, Neulussheim; Kurt Schilling, Schwetzingen, all of Fed. Rep. of Germany

[73] Assignee: Bayer Aktiengesellschaft, Leverkusen, Fed. Rep. of Germany

[21] Appl. No.: 336,861

[22] Filed: Apr. 12, 1989

[30] Foreign Application Priority Data

Apr. 27, 1988 [DE] Fed. Rep. of Germany ....... 3814163

[51] Int. Cl.$^5$ ............................................. C07C 319/24
[52] U.S. Cl. ........................................ 568/26; 568/22; 568/25
[58] Field of Search ............................ 568/22, 25, 26

[56] References Cited

U.S. PATENT DOCUMENTS 3,992,432 11/1976 Napier et al. ...................... 558/344

FOREIGN PATENT DOCUMENTS 104474 9/1973 Japan .

OTHER PUBLICATIONS

Houben-Weyl, Methoden der Organischen Chemie, Band E 11, 135–142, herausgegeben von K. H. Buchel et al.

Primary Examiner—Mary E. Ceperley
Attorney, Agent, or Firm—Connolly and Hutz

[57] ABSTRACT

A process for the production of diorganodisulfides by oxidation of meraptans in which the mercaptan is reacted with a halogen compound capable of releasing at least one halogen atom and taking up a hydrogen atom instead, the reaction being carried out at 0° to 100° C. in the presence of base and, optionally, a phase transfer catalyst.

6 Claims, No Drawings

PROCESS FOR THE PRODUCTION OF DISULFIDES

Diorganodisulfides and their production by oxidation of corresponding mercaptans are known, cf. Houben-Weyl, Methoden der organischen Chemie, Vol. C11/1, page 133, Georg Thieme Verlag, 1985. Oxidizing agents which have been used include, for example, oxygen, hydrogen peroxide, chlorine, bromine, iodine, hypochlorite, hypobromite, hypoiodite, iron(III) chloride, potassium hexacyanoferrate(III) and nitric oxide. However, none of these oxidizing agents is satisfactory. Either they give poor yields or the reaction is difficult to control (for example where hydrogen peroxide is used) or secondary products are formed in large quantities (for example where elemental halogens and hydrogen peroxide are used).

The present invention relates to a process for the production of diorganodisulfides by oxidation of mercaptans which is characterized in that the mercaptan is reacted with a halogen compound which is capable of releasing at least one halogen atom and taking up a hydrogen atom in its place, the reaction being carried out at a temperature of 0° to 100° C. in the presence of a base and, optionally, a phase transfer catalyst.

The process is preferably carried out in aqueous medium. In this case, the reaction takes place in heterogeneous phase. The reaction may also be carried out in homogeneous phase, for example in an organic solvent or in the absence of a solvent. Suitable solvents are, in particular, alcohols or the halogen compounds used for the oxidation. Where the reaction is carried out in homogeneous phase, tertiary amines are preferably used as the bases. The base is generally used in quantities of at least 0.5 mol per mol mercaptan. An excess of base does not affect the reaction. The phase transfer catalyst is used in catalytically active quantities, i.e. generally in quantities of about 0.5 to 10 millimol per mol mercaptan. The halogen compound may be used in excess, although substantially stoichiometric quantities, for example approximately 0.5 mol and preferably 0.3 to 0.7 mol per mol mercaptan are generally sufficient.

The process according to the invention enables diorganodisulfides to be obtained in high yields and high purity under very mild reaction conditions.

The reaction according to the invention may be illustrated, for example, by the following reaction equation:

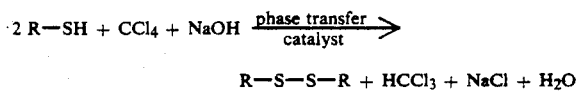

$$R-S-S-R + HCCl_3 + NaCl + H_2O$$

The process according to the invention may generally be carried out by initially introducing the mercaptan, the base and the phase transfer catalyst in an aqueous medium or an organic medium or even with no solvent and slowly adding the halogen compound. The reaction may be started at room temperature, beginning immediately and proceeding exothermically, so that the addition rate may be used to control the reaction temperature. The reaction mixture may of course be cooled or even heated as necessary. In the case of a heterogeneous system, the reaction mixture has to be kept in motion during the reaction. The same is recommended for the other embodiments, for example by stirring. On completion of the reaction carried out in aqueous medium, the aqueous phase may be separated from the organic phase and the organic phase, which consists essentially of diorganodisulfide and reduction product of the halogen compound, may be purified in known manner, for example by distillation. Where the reaction is carried out in homogeneous phase, the amine hydrochloride formed may be separated off and the organic phase worked up, for example by distillation.

The reaction is generally carried out at temperatures of 0° to 100° C., preferably at temperatures of 20° to 65° C. and more preferably at temperatures of 20° to 35° C. The diorganodisulfides produced in accordance with the invention are mostly liquid at room temperature or are low-melting solids.

Mercaptans suitable for the process are, primarily, alkyl mercaptans (linear or branched), preferably containing 1 to 18 and more preferably 1 to 12 carbon atoms. Other suitable mercaptans are aralkyl mercaptans, such as benzyl mercaptan, or substituted mercaptans, such as mercaptoalkanols (mercapto-ethanol), or mercaptocarboxylic acid esters, such as mercapto-propionic acid ester, mercapto acetic acid ester. It is also possible to use mercaptans containing several SH groups, for example $\alpha,\omega$-dimercaptoalkanes preferably containing 2 to 6 carbon atoms, such as 1,2-dimercaptoethane, 1,3-dimercaptopropane and also $\beta$-mercaptopropionic acid tristrimethylol propane ester and $\beta$-mercaptopropionic acid tetra-pentaerythritol ester. Disulfides containing several —S—S—groups up to and including polymers are formed from starting products such as these. The chain length of such products may be regulated by the co-use of monofunctional mercaptans. Mixtures of mercaptans may of course also be reacted. It follows from this that the substituent R in the reaction equation shown above is preferably an alkyl radical, more preferably an alkyl radical containing 1 to 18 or 1 to 12 carbon atoms, and a corresponding hydroxyalkyl radical or even a carboxylic acid radical. The substituents R can also be different. The possibilities of differences are given by the above mentioned examples of different mercapto compounds.

The halogen compounds by which the mercaptans are oxidized must be capable of releasing a halogen atom and taking up a hydrogen atom. Suitable halogen compounds are, for example, tetrachloromethane, tetrabromomethane, trichlorobromomethane, bromoform, iodoform, 1,1-dichloro-2-bromomethane, symmetrical tetrachlorodibromomethane, pentachloroethane, hexachloroethane, octachloropropane, decachlorobutane. Generally speaking, therefore, the halogen compounds in question are halogenated, more especially chlorinated, brominated or iodized, preferably saturated, hydrocarbons containing 1 to 6 carbon atoms which are generally perhalogenated or, at all events, contain only 1 or 2 hydrogen atoms.

Suitable bases are inorganic bases, such as alkali hydroxides, alkali carbonates, alkaline earth hydroxides, or organic bases, such as tertiary amines. They may be used in solid form or as aqueous solutions. Examples are sodium hydroxide, potassium hydroxide, sodium carbonate, potassium carbonate, barium hydroxide, calcium hydroxide, triethylamine, N,N-dimethyl cyclohexylamine, N,N-dimethyl benzylamine. Sodium hydroxide is preferred.

Preferred phase transfer catalysts are quaternary ammonium salts and quaternary phosphonium salts. Examples are tetrabutyl ammonium bromide, benzyl trimethyl ammonium chloride, tricapryl methyl ammonium chloride, benzyl triphenyl phosphonium bromide, tributyl hexadecyl phosphonium bromide.

The process according to the invention is illustrated by the following Examples.

EXAMPLE 1

160 g (1 mol) tert.-nonyl mercaptan, 22 g (0.55 mol) sodium hydroxide, 75 ml. water and 0.8 g 2 mmol) tricapryl methyl ammonium chloride are introduced into a 3-necked flask equipped with a stirrer, reflux condenser and dropping funnel.

77 g (0.5 mol) tetrachloromethane are then added dropwise over a period of 1 hour while stirring and cooling with water, the temperature rising from 20° to 30° C. The mixture is then stirred for 2 hours, after which the aqueous phase is separated from the organic phase in a separation funnel. The organic phase is freed from the chloroform formed and from residual moisture in a water jet vacuum at 90° C. and filtered. Yield of di-tert.-nonyl disulfide: 155.5 g (98.4%).

EXAMPLE 2

202 g (1 mol) n-dodecyl mercaptan, 22 g (0.55 mol) sodium hydroxide, 100 ml water and 0.6 g (1.5 mmol) tricapryl methyl ammonium chloride are reacted as in Example 1 with 77 g (0.5 mol) tetrachloromethane. Yield of di-n-dodecyl disulfide: 198 g (99%).

EXAMPLE 3

720 g (8 mol) tert.-butyl mercaptan, 501.3 g (5.33 mol) ethane-1,2-diol, 392 g (9.8 mol) sodium hydroxide, 1330 ml water and 3.1 g (7.75 mmol) tricapryl methyl ammonium chloride are reacted as in Example 1 with 1437.3 g (9.33 mol) tetrachloro-methane. Yield of "mixed disulfide" of formula I: 1178 g (98.6%)

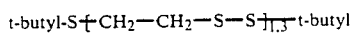

Formula I

We claim:

1. A process for the production of diorganodisulfides by oxidation of mercaptans wherein the mercaptan is reacted with halogenated hydrocarbons containing 1 to 6 carbon atoms which contain at most two hydrogen atoms at a temperature from 0° to 100° C. in the presence of alkali hydroxide or alkaline earth hydroxide and, optionally, a phase transfer catalyst.

2. A process as claimed in claim 1, characterized in that a $C_1$–$C_{18}$ alkyl mercaptan is used as the mercaptan.

3. A process as claimed in claim 1, characterized in that an α,ω-dimercaptoalkane containing 1 to 16 C atoms, optionally together with a $C_1$–$C_{18}$ alkyl mercaptan, is used as the mercaptan.

4. A process as claimed in claim 1, characterized in that carbon tetrachloride is used as the halogen compound.

5. A process as claimed in claim 1, characterized in that sodium hydroxide is used as the base.

6. A process as claimed in claim 1, characterized in that the reaction is carried out in aqueous medium.

* * * * *